United States Patent [19]

Guggenheim

[11] Patent Number: 5,404,763
[45] Date of Patent: Apr. 11, 1995

[54] POLYPORT ATMOSPHERIC GAS SAMPLER

[75] Inventor: S. Frederic Guggenheim, Teaneck, N.J.

[73] Assignee: The United States of America as represented by the Department of Energy, Washington, D.C.

[21] Appl. No.: 87,550

[22] Filed: Jul. 8, 1993

[51] Int. Cl.⁶ .............................................. G01N 1/24
[52] U.S. Cl. ................................................. 73/863.31
[58] Field of Search ........... 73/863.01, 863.21, 863.23, 73/863.25, 863.31, 863.33, 863.71, 864.34, 864.31

[56] References Cited

U.S. PATENT DOCUMENTS

| | | | |
|---|---|---|---|
| 2,906,125 | 9/1959 | Jewett, Jr. | 73/864.31 |
| 3,355,940 | 12/1967 | Pannetier | 73/864.31 |
| 3,884,081 | 5/1975 | Griffith | 73/863.31 |
| 4,116,067 | 9/1978 | Pankratz et al. | 73/863.31 |
| 4,226,115 | 10/1980 | Williams | 73/863.23 |
| 4,584,887 | 4/1986 | Galen | 73/863.31 |
| 4,869,117 | 9/1989 | McAndless et al. | 73/864.34 |

Primary Examiner—Robert Raevis
Attorney, Agent, or Firm—Daniel D. Park; Thomas G. Anderson; William R. Moser

[57] ABSTRACT

An atmospheric gas sampler with a multi-port valve which allows for multiple, sequential sampling of air through a plurality of gas sampling tubes mounted in corresponding gas inlet ports. The gas sampler comprises a flow-through housing which defines a sampling chamber and includes a gas outlet port to accommodate a flow of gases through the housing. An apertured sample support plate defining the inlet ports extends across and encloses the sampling chamber and supports gas sampling tubes which depend into the sampling chamber and are secured across each of the inlet ports of the sample support plate in a flow-through relation to the flow of gases through the housing during sampling operations. A normally closed stopper means mounted on the sample support plate and operatively associated with each of the inlet ports blocks the flow of gases through the respective gas sampling tubes. A camming mechanism mounted on the sample support plate is adapted to rotate under and selectively lift open the stopper spring to accommodate a predetermined flow of gas through the respective gas sampling tubes when air is drawn from the housing through the outlet port.

16 Claims, 5 Drawing Sheets

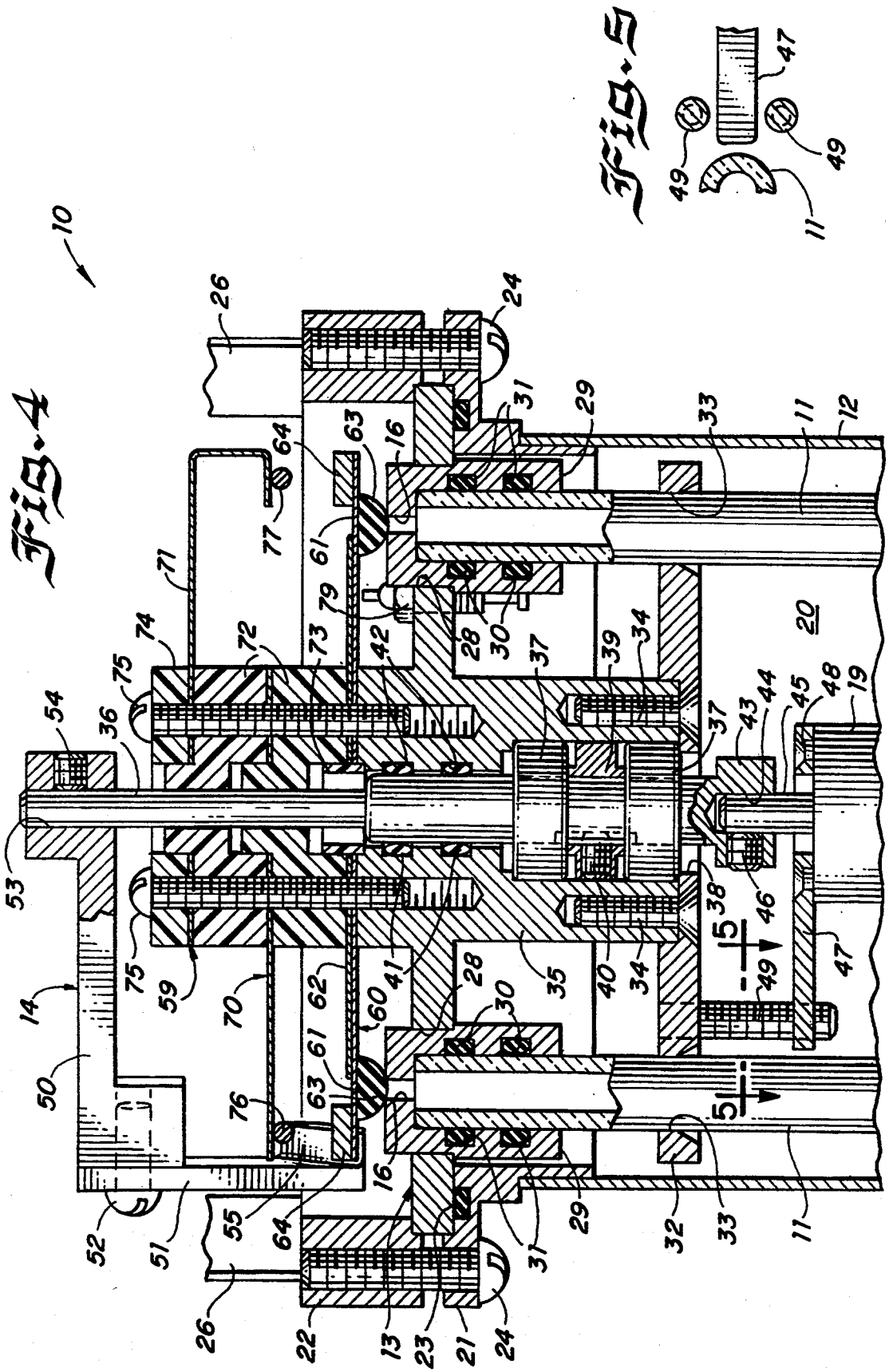

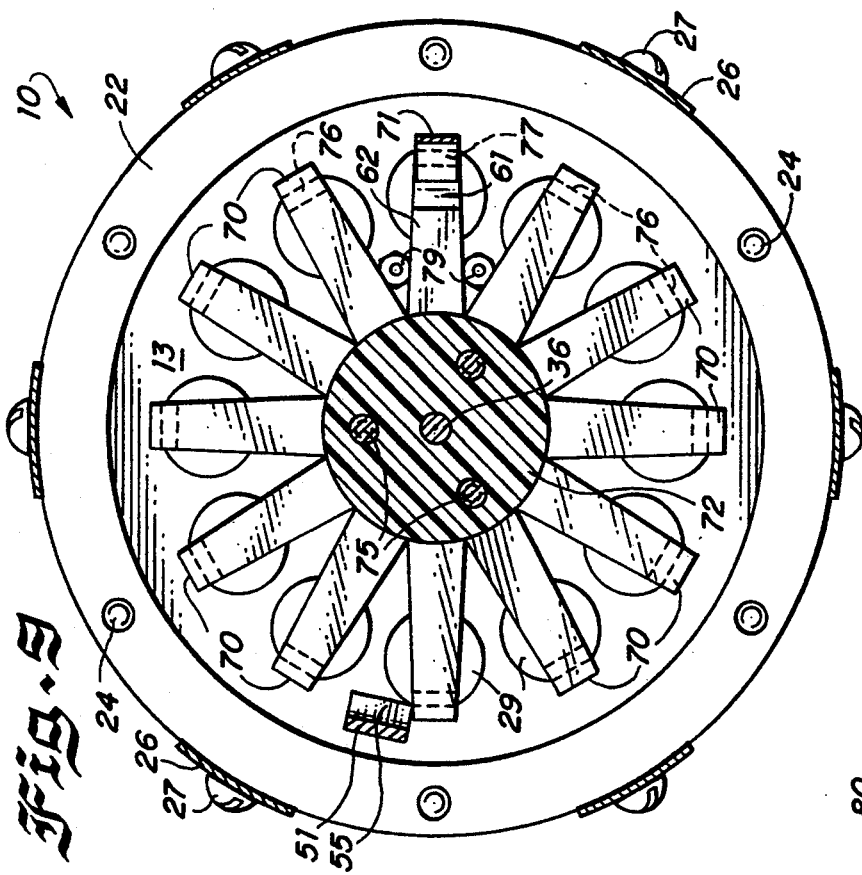
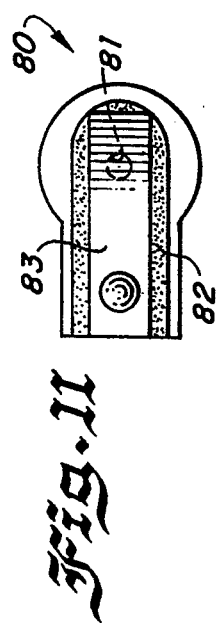
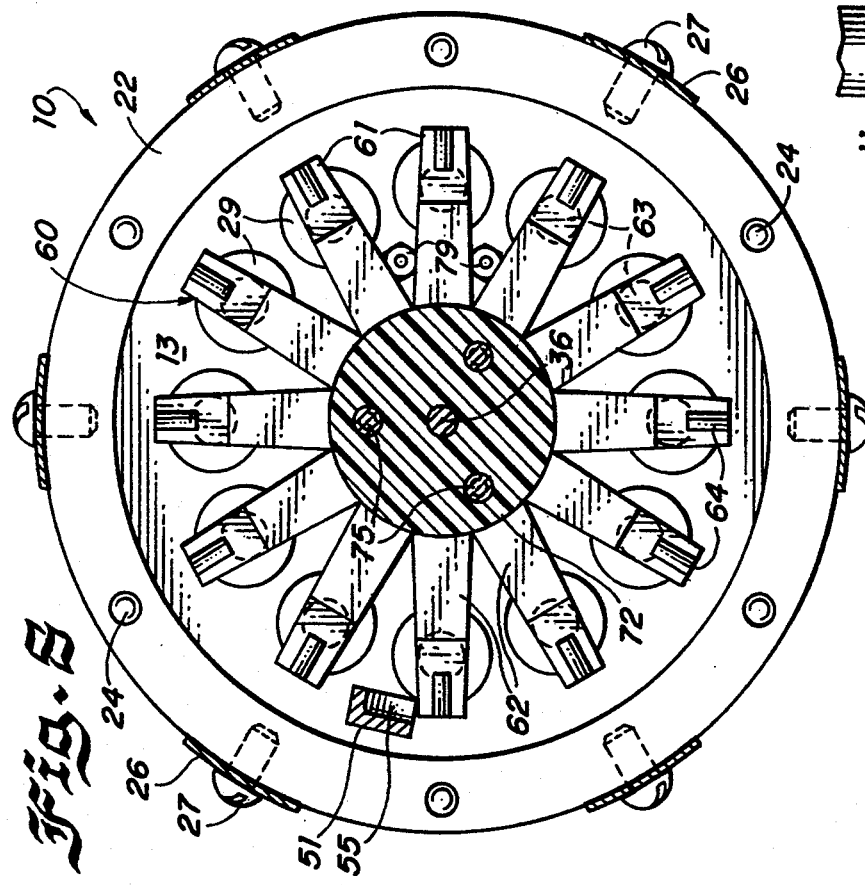
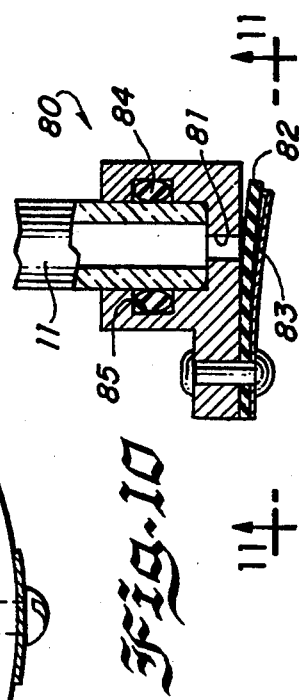

POLYPORT ATMOSPHERIC GAS SAMPLER

BACKGROUND OF THE INVENTION

The present invention relates to a gas sampling device, and, more particularly, to an atmospheric gas sampler with a multi-port valve which allows for multiple, sequential sampling of air through a plurality of sample tubes mounted in corresponding ports.

Small and lightweight atmospheric gas samplers are useful in conducting various environmental, meteorological and atmospheric tests. Whether for detecting hazardous contaminants or studying the atmosphere, gas samplers are essential for collecting or detecting various gases, aerosols and other particulates in the atmosphere. Typically, sampling is conducted by drawing air through a sample tube containing certain adsorbents which trap the target gases or particulates. These adsorbed gases or particulates are then later analyzed in the laboratory. As these studies have become more complex, there has been an increasing need, not only to take large numbers of samples, but also to take samples at various locations, times, and altitudes. Accordingly, there is a need for samplers which can take numerous gas samples efficiently and accurately, and whose functions can be automated.

The need for a compact, lightweight and efficient gas sampler is especially important in various atmospheric and meteorological studies. In atmospheric transport studies, a tracer gas, in the form of a perfluorocarbon, is released in predetermined amounts from various preselected positions. The tracer gas is then collected by gas samplers deployed at various locations and analyzed to examine atmospheric transport properties. In gas dispersion studies, certain gases or aerosols are selectively sampled at various locations and altitudes to determine their concentrations and to characterize their vertical structure or profile. These and other related experiments have been used to validate models describing atmospheric transport and dispersion of pollutants.

To perform such atmospheric experiments, gas samplers are normally attached to balloon tetherlines and lofted to various altitudes to take samples. In such applications, the gas samplers must be small and lightweight so that several samplers can be taken up together. Ideally, each gas sampler should accommodate multiple sample tubes so that many air samples can be taken at one lofting. Previously, however, gas samplers usually contained only a single adsorbent sample tube such that the balloon had to be hauled down after each sampling. Some gas samplers have the capability to take multiple samples, but these were typically heavy, complicated and not conducive to automated operation. What is needed is a simple, lightweight gas sampler which can take multiple samples and whose operation can be fully automated.

In view of the foregoing, the general object of this invention is to provide an atmospheric gas sampler with a multi-port valve which allows successive sampling of air through a plurality of sample tubes mounted in corresponding ports.

Another object of this invention is to provide a self-contained and fully automated gas sampler including unique electrical switches that provide reliable signals to an electrical control system that a port has been opened or closed.

Yet another object of this invention is to provide a gas sampler with a nozzle or check valve that prevents back-flow of air into the sample tubes.

Additional objects, advantages and novel features of the invention will become apparent to those skilled in the art upon examination of the following and by practice of the invention.

SUMMARY OF THE INVENTION

To achieve the foregoing and other objects, this invention provides an atmospheric gas sampler with a multi-port valve which allows for multiple, sequential sampling of air through a plurality of gas sampling tubes mounted in corresponding inlet ports by successively drawing air through each of the inlet ports. This configuration allows for the multiple sampling of air without the need for removal and replacement of the gas sampling tubes between each air sample.

The multi-port gas sampler of the present invention comprises a flow-through housing which defines a sampling chamber and includes a gas outlet means to accommodate a flow of gases through the housing. An apertured sample support plate defining the inlet ports extends across and encloses the sampling chamber and supports gas sampling tubes which depend into the sampling chamber and are secured across each of the inlet ports of the sample support plate in a flow-through relation to the flow of gases through the housing during sampling operations. A normally closed stopper means mounted on the sample support plate and operatively associated with each of the inlet ports blocks the flow of gases through the respective gas sampling tubes. A camming mechanism mounted on the sample support plate is adapted to rotate under and selectively lift open the stopper spring to accommodate a predetermined flow of gases to be sampled through the respective gas sampling tubes.

A signalling means mounted on the sample support plate and aligned with the stopper spring senses the opening of the stopper means and sends a signal to an electrical control system that the stopper means has been opened. The electrical control system receives the signal from the signalling means and selectively operates a drive motor which in turn rotates the camming mechanism to selectively and successively open the stopper means associated with each gas sampling tube to accommodate a flow of gases through the corresponding gas sampling tube and the flow-through housing.

In an alternative embodiment, a check valve is positioned over each of the open ends of the gas sampling tube to retard the flow of gases into the gas sampling tubes from the gas sampling chamber to essentially isolate the sampling tubes when its respective stopper means is in its normally closed position. When the stopper means is open, however, the check valve opens to allow the gases to flow through the respective gas sampling tubes.

BRIEF DESCRIPTION OF THE DRAWINGS

The present invention is illustrated in the accompanying drawings where:

FIG. 4 is an enlarged cross-sectional view of the gas sampler showing the multi-port assembly in greater detail;

FIG. 5 is a cross-sectional view of the gas sampler taken substantially along line 5—5 in FIG. 4 showing the motor arm captured between two screws;

FIG. 8 is a cross-sectional view of the gas sampler taken substantially along line 8—8 in FIG. 2 showing the stopper spring in greater detail.

FIG. 9 is a cross-sectional view taken substantially along line 9—9 in FIG. 2;

FIG. 10 is a cross-sectional view of an alternate embodiment of the invention wherein a check valve is used; and FIG. 11 is an end view taken substantially along line 11—11 in FIG. 10.

DESCRIPTION OF THE PREFERRED EMBODIMENT

Figure 1:
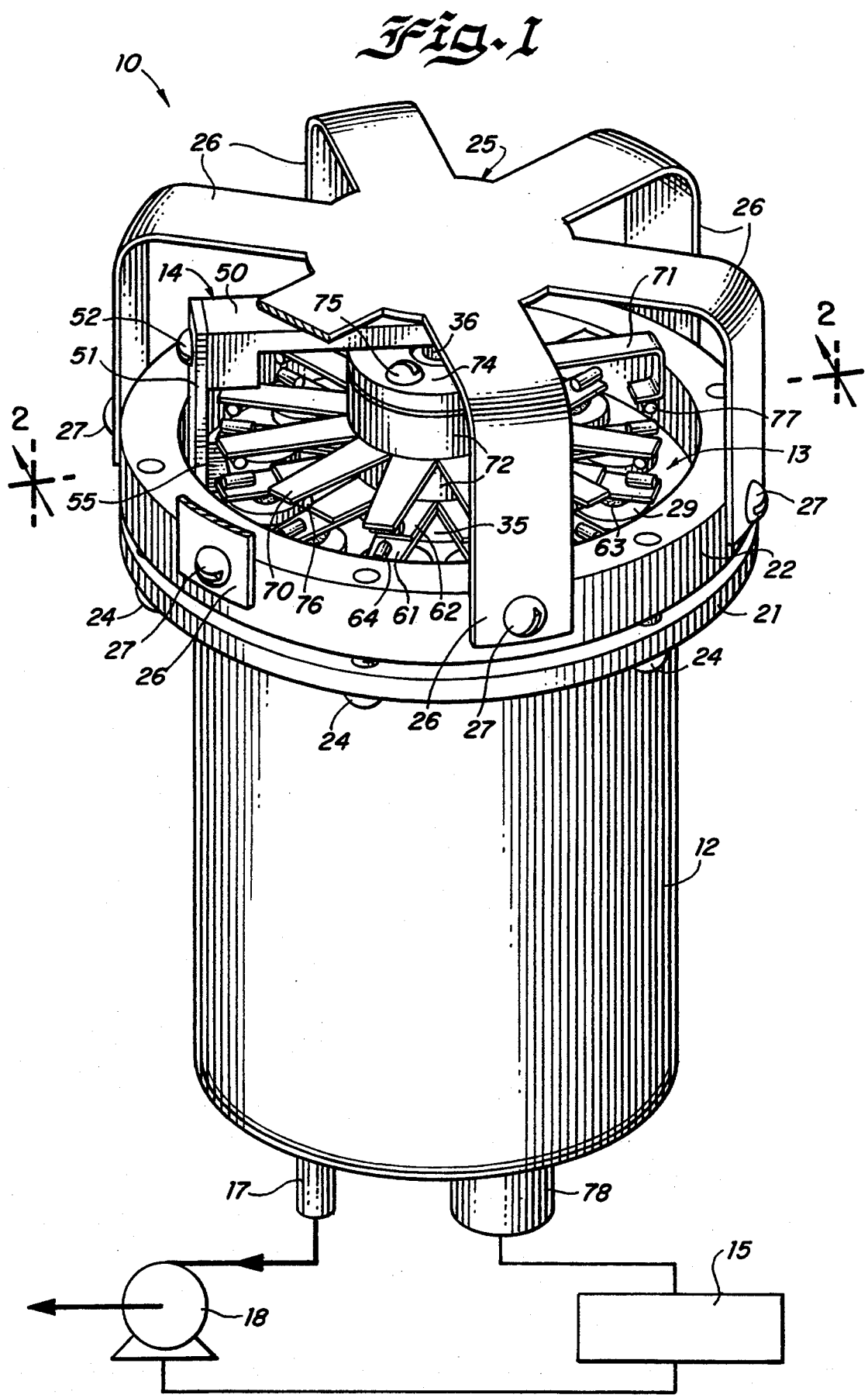
FIG. 1 is a pictorial view of the multi-port gas sampler of the present invention connected to an electrical control system and a pumping device.
Figure 2:
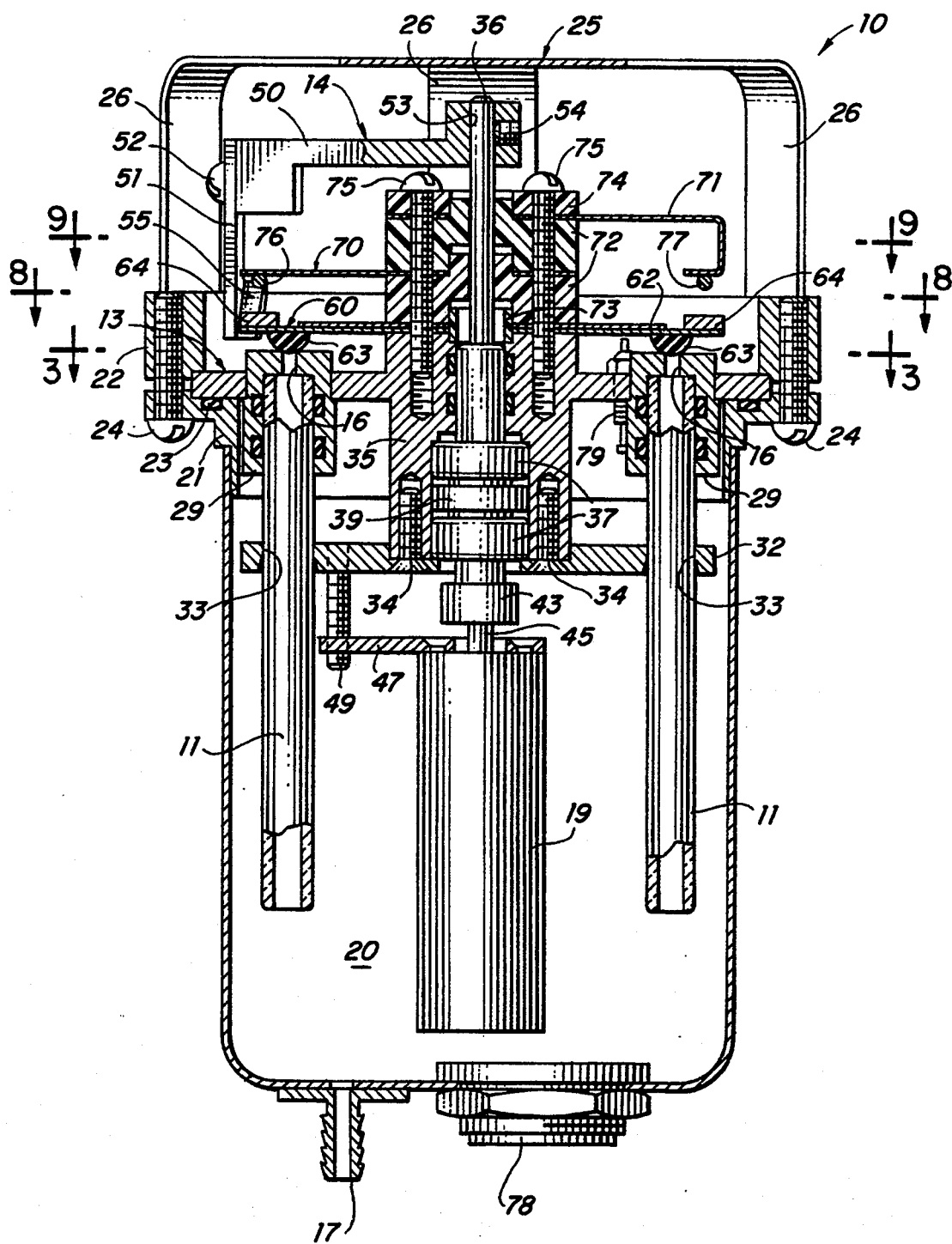
FIG. 2 is a cross-sectional view of the multi-port gas sampler taken substantially along line 2—2 in FIG. 1.

Referring to FIGS. 1 and 2, the multi-port gas sampler 10 embodying the invention includes a plurality of air sample tubes 11 adapted to retain a suitable adsorbent material or other suitable gas sampling media suspended within a cylindrical canister 12 from a tube support plate 13 which encloses the sample tubes 11 within the canister 12. As will be described, the invention accommodates the collection of multiple air samples by sequentially drawing ambient air through each of the respective air sample tubes 11 during the course of the sampling without necessitating disassembly of the device and the removal and replacement of adsorbent material between samples. In the embodiment shown, a rotating camming mechanism 14 activated by an electrical control system 15 is used to sequentially open each of twelve normally closed inlet ports 16 which are each associated with a respective sample tube 11 as ambient air is drawn through the inlet ports 16 and out of the canister 12 through an outlet port 17 provided in the base of the canister which is in turn connected to a suitable vacuum pump 18 or the like.

As shown in the drawings, the canister 12 is cup-shaped with an open and a closed end. The open end of the canister 12 is closed off by a circular tube support plate 13 to enclose the sample tubes 11 and a drive motor 19 within the interior 20 of the canister 12. The tube support plate 13 is attached to the canister 12 by means of an outwardly projecting canister flange 21 and a ring-shaped guard flange 22. The canister flange 21, being similarly ring-shaped, encircles the periphery of the open end of the canister 12 to form a shoulder sized to cooperate with the tube support plate 13 to enclose the cylindrical open end of the interior 20 of the canister 12. The canister flange 21 is affixed to the canister 12 by means of an epoxy adhesive or other well known means to form an air tight seal between the canister 12 and the canister flange 21, and a conventional o-ring 23 is provided between the tube support plate 13 and the canister flange 21 to further seal the canister interior 20 from the ambient atmosphere. As can be readily appreciated, the tube support plate 13 is secured into position by the guard flange 22 which is in turn secured to the canister flange 21 by a plurality of machine screws 24 extending through the canister flange 21 and threaded into the guard flange 22 about its periphery to effectively clamp the tube support plate 13 between the flanges 21 and 22.

A spider-shaped guard cage 25 is mounted over the tube support plate 13 over the upper end of the canister 12 to protect the external parts of the gas sampler 10 while allowing air to pass freely to the inlet ports 14. As shown in FIG. 1, the guard cage 25 includes a plurality of outwardly projecting arms 26 which are bent in a downward manner and connected to the guard flange 22 by means of screws 27.

Figure 3:
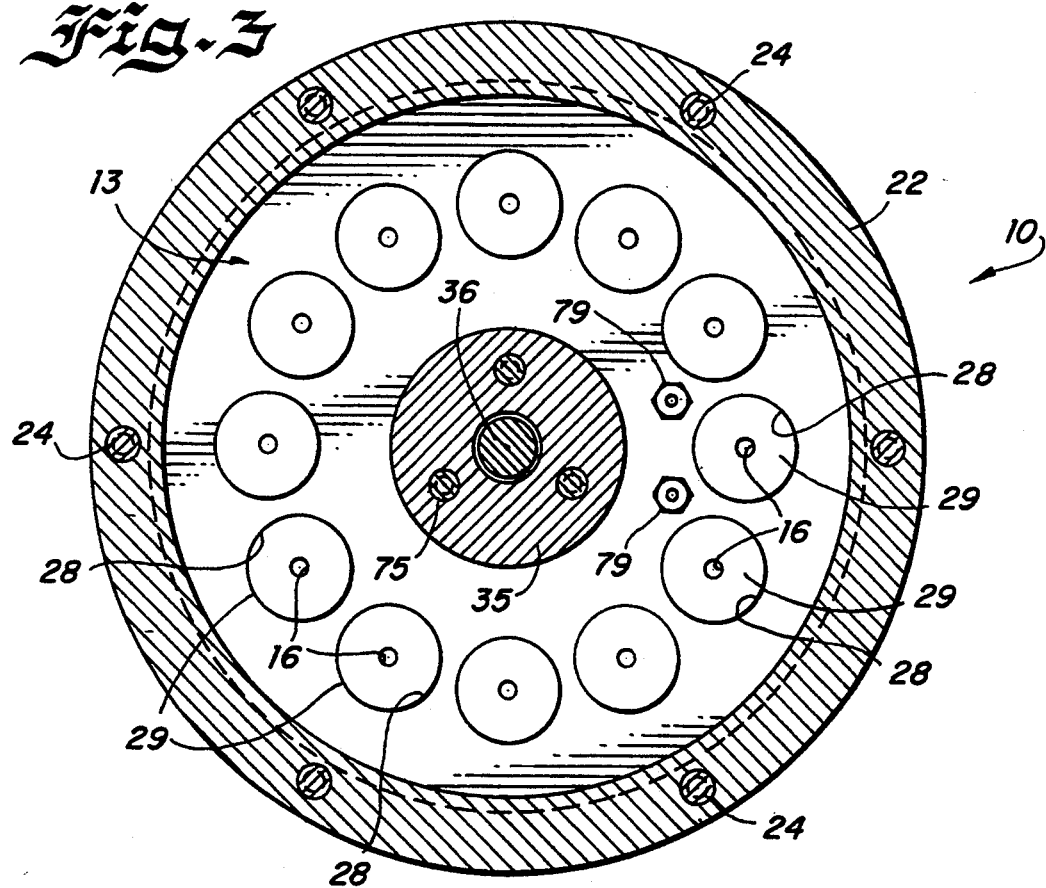
FIG. 3 is a cross-sectional view of the gas sampler taken substantially along line 3—3 in FIG. 2 showing the tube support plate in detail.

Referring to FIGS. 3 and 4, the tube support plate 13 includes a plurality of circular holes 28 arranged concentrically about its periphery. Within each hole 28, a sample tube 11 of predetermined length is positioned such that the sample tube 11 extends into the canister interior 20 with one end of the sample tube being flush with the tube support plate 13 and the opposed end being open to the canister interior 20.

As shown in greater detail in FIG. 4, the sample tubes 11 are retained within the holes 28 of the tube support plate 13 by a plurality of annular sleeves or collars forming sample tube seals 29 which firmly hold the sample tubes 11 in place and provide an air-tight seal between the tube support plate 13 and the sample tubes 11. Each sample tube seal 29 is generally cylindrically shaped and includes an open and a closed end, with the closed end having a small circular hole or inlet port 16 which allows ambient air to flow into its respective sample tube 11. The sample tube seals 29 are positioned within the holes 28 of the tube support plate 13 with the open ends of the sample tube seals 29 extending inwardly into the canister interior 20 and the closed ends extending outwardly and protruding slightly above the tube support plate 13. The outer diameter of the sample tube seals 29 is sized to fit into the holes 28 of the tube support plate 13 such that, when an adhesive is used to securely join each of the sample tube seals 29 to the tube support plate 13, an air tight seal is formed between each of the seals 29 and the support plate 13.

The open end of the sample tube seal 29 is sized to receive and securely hold a sample tube 11 in place. The sample tube 11 is removably inserted into the open end of the sample tube seal 29 such that one end of the sample tube 11 is adjacent the closed end of the sample tube seal 29. Two resilient o-rings 30, positioned in annular interior grooves 31 in each of the sample tube seals 29, ensure that air tight seals are formed between the sample tubes 11 and the sample tube seals 29.

A tube guide 32 aligns and supports the plurality of sample tubes 11 within the canister interior 20. The tube guide 32 is a circular disk including a plurality of circular holes 33 arranged concentrically and in axial alignment with the holes 28 of the tube support plate 13. The holes 33 of the tube guide 32 are sized to slidably hold the sample tubes 11 to facilitate removal of the sample tubes 11 after sampling. The tube guide 32 is secured to the tube support plate 13 by screws 34 located in the central area of the tube guide 32.

Referring again to FIGS. 3 and 4, the tube support plate 13 includes a central cylindrical housing 35 which accommodates a motor shaft extension 36, which rotatably fits into the housing 35 and extends through the housing 35. The housing 35 is integrally formed or connected with the tube support plate 13 and extends generally downward into the canister interior 20, while a portion extends slightly above the tube support plate 13. As can be seen from FIG. 4, the inner diameter of the lower portion of the housing 35 is slightly enlarged to receive and retain annular ball bearing assemblies 37 which in turn carry the motor shaft extension 36 and facilitate its rotation within the base plate housing 35. The annular ball bearing assemblies 37 are retained within the lower portion of the base plate housing 35 by the tube guide 32. As indicated in FIG. 4, the diameter of a central clearance hole 38 provided in the tube guide 32 for the motor shaft extension 36 is slightly smaller than the outer diameter of the annular ball bearing assemblies 37, so that the tube guide 32 effectively supports the bearing assemblies 37 within the housing 35. In this connection, it should be noted that a bearing spacer 39, attached to the motor shaft extension 36 by means of a set screw 40, separates the two bearing assemblies 37 and prevents axial movement of the motor shaft extension 36. Similarly, a pair of resilient o-rings 41 are positioned in annular interior grooves 42 in the upper portion of the housing 35 to prevent leakage of ambient air into the canister interior 20 as the motor shaft extension 36 is rotated during operation of the gas sampler 10.

The lower end of the motor shaft extension 36 includes a short cylindrical base portion 43 wherein a drive motor 19 attached. The base portion 43 includes a bore 44 wherein the shaft 45 of the drive motor 19 is inserted and secured by set screws 46 threaded into the base portion 43. A motor arm 47 is attached to the drive motor 19 by screws 48 and is positioned between two screws 49 extending downwardly from the tube guide 32, as shown in FIG. 5. The motor arm 47 is captured in the manner shown to prevent rotation of the body of the drive motor 19 and to keep the motor 19 from binding up. In the embodiment, shown, the drive motor 19 is a lightweight, high-torque DC motor readily available from a variety of commercial manufacturers.

Referring to FIGS. 4 and 8, a stopper spring 60 is mounted to the upper end of the central cylindrical housing 35 of the tube support plate 13. The stopper spring 60 includes a circular central area from which extends a plurality of fingers 61 forming leaf springs which are aligned directly over the corresponding inlet ports 16 of the sample tubes seals 29. In the preferred embodiment, the stopper spring 60 includes twelve fingers 61 which correspond to the twelve sample tubes 11, and as shown in FIG. 7, each of the fingers 61 is reinforced or rigidified with an additional leaf spring affixed to the top of the fingers 61 as shown at 62.

Each finger 61 of the stopper spring 60 includes a hemispherically-shaped stopper 63 secured by a suitable adhesive to the underside of each finger 61. These stoppers 63 are each positioned directly above and biased against the inlet port 16 of a respective sample tube 11 by the stopper spring 60 such that an air tight seal exists between the stopper 63 and the inlet port 16 when the stopper spring 60 is in its normal unraised position. In the embodiment shown, the stopper 63 is molded from a relatively elastic and resilient silicon/rubber material adequate to produce a tight seal between the stopper 63 and the inlet port 16 when the stopper 63 is in its normally closed position.

Referring again to FIG. 2, the upper end of the motor shaft extension 36 supports and rotates the camming mechanism 14 which includes a lift arm 50 and a lifter 51 joined by screws 52. The lift arm 50 includes a circular hole 53 which fits over the end of the motor shaft extension 36 and is secured by a set screw 54 inserted perpendicular to the hole. The lifter 51 includes an angled ramp or cam 55 which when rotated under the stopper spring 60 engages and lifts the ends or fingers 61 of the stopper spring 60 to open the inlet ports 16 as will be described. This lifting arrangement is illustrated in greater detail in FIGS. 6 and 7 which show an enlarged view of the camming mechanism 14 as it is rotated under one of the fingers 61 of the stopper spring 60 to disengage its respective stopper 63 from its associated inlet port 16 to accommodate the flow of ambient air through the sample tube 11 depending beneath it.

Figure 6:
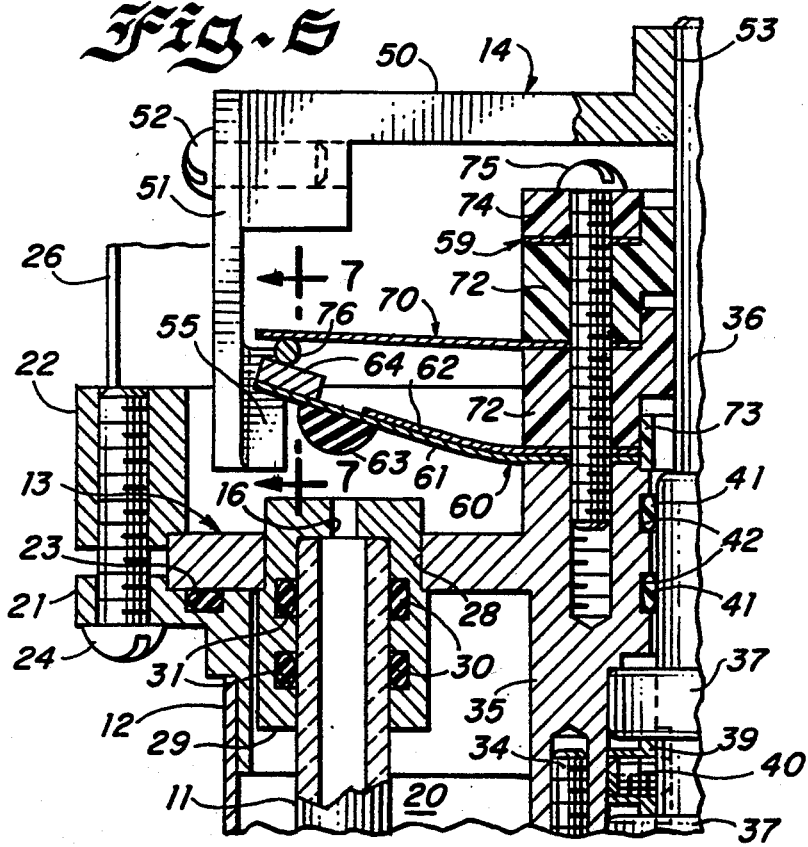
FIG. 6 is an enlarged cross-sectional view of the gas sampler showing the lifting and switching mechanism of the sampler in greater detail.
Figure 7:
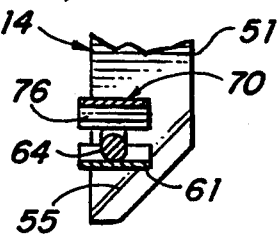
FIG. 7 is a cross-sectional view taken substantially along line 7—7 in FIG. 6 showing the lifting mechanism.

Referring now to FIGS. 6–8, small metal contacts 64 are soft soldered to the end of each finger 61 on the upperside of the stopper spring 60 so as to insure good electrical contact between the stopper spring 60 and a lower contact spring 70 and an upper contact spring 71 when the finger 61 is raised, as shown in the drawings. Preferably, the stopper spring 60, as well as the lower contact spring 70 and the upper contact spring 71, is made from a durable and flexible conducting metal such as beryllium copper.

Referring to FIGS. 2 and 9, the lower contact spring 70 and the upper contact spring 71 are respectively positioned above the stopper spring 60 being interspaced by annular leaf spacers 72 which separate and electrically insulate the springs 70 and 71. A small, ring-shaped locating cylinder 73, as shown more clearly in FIG. 4, is positioned above the cylindrical housing 35 of the tube support plate 13 to center the stopper spring 60 and the spring leaf spacers 72. An annular top insulator 74 overlays the upper contact spring 59, and the entire assembly is secured by screws 75 to the tube support plate 13.

The lower contact spring 70 includes a plurality of outwardly extending fingers wherein small metal contacts 76 are positioned so as to insure good electrical connection between the lower contact spring 70 and the stopper spring 60. In the embodiment described herein, the lower contact spring 70 includes eleven fingers which are respectively aligned directly above the corresponding fingers 61 of the stopper spring 60. The upper contact spring 71 includes one outwardly extending finger which is positioned over and directly aligned with the twelfth or last finger 61 of the stopper spring 60 which is not overlaid by the lower contact spring 70. The finger of the upper contact spring 71 is bent downward and inward with a metal contact 77 soldered to the lower end of the finger to insure a good electrical connection between the upper contact spring 71 and the stopper spring 60 when the twelfth finger of the stopper spring 60 is raised.

Referring to FIGS. 1 and 2, an electrical connector 78 attached to the base of the canister 12 provides the necessary electrical connections from the electrical control system 15 to the gas sampler 10 of the present invention. The connector 78 provides electrical connections to the drive motor 19, the lower contact spring 70, and the upper contact spring 71, as well as providing the necessary grounding for the sampler 10. The electrical connections are made with suitable wires (not shown), and as shown more clearly in FIG. 4, air-tight insulated terminals 79 are used to pass the wires through the tube support plate 13, so that the canister interior 20 is essentially isolated from ambient air except through the inlet ports 16 as they are sequentially opened during sampling operations.

In operation, the gas sampler 10 of the present invention makes multiple, sequential sampling of the atmosphere by successively opening the normally closed inlet ports 16 while drawing air out of the canister 12 through the outlet port 17. The gas sampler 10 is controlled by the electrical control system 15 which activates the drive motor 19 which in turn, via the motor shaft extension 36, rotates the camming mechanism 14 (counterclockwise when viewed from the top in FIG. 2) to a finger 61 of the stopper spring 60 located above a corresponding sample tube 11. The lifting action provided by the ramp or cam 55 on the lifter 51 raises the finger 61 of the stopper spring 60 to open the corresponding inlet port 16 which allows ambient air to flow through the corresponding sample tube 11. This process is continued until all of the sample tubes 11 of the gas sampler 10 have been exposed to the atmosphere. Sampling is usually conducted during ascent of the gas sampler 10 into the atmosphere, and typically, the last or twelfth sample tube 11 is packed with an adsorbent and left open during decent to allow ambient air to flow back into the canister 12 to equalize the canister interior 20 pressure with that of ambient pressure.

The signalling for the opening and closing of the inlet ports 16 is achieved by applying a voltage to the lower contact spring 70 and the upper contact spring 71 while properly grounding the stopper spring 60. Initially, when a finger 61 of the stopper spring 60 is raised and makes contact with the lower contact spring 70 an electrical circuit is closed to send a positive signal to the electrical control system 15 that an inlet port 16 has been opened. The signal acts as a switch to stop the drive motor 18 and allow the inlet port 16 to stay open to sample the air. After sampling the atmosphere for a predetermined amount of time, the control system 15 sends a signal causing the motor 19 to rotate the camming mechanism to the next sequential sample tube 11. Typically, this process is continued until the finger 61 corresponding to the last sample tube 11 (the twelfth sample tube in the preferred embodiment) is reached. When that last finger 61 is raised, an electrical circuit is closed with the upper contact spring 71 to send a signal to the control system 15 that the last or twelfth sample tube 12 has been exposed to air and that the sampling process may be ended.

From the foregoing, it can be seen that the outlet ends of the sample tubes 11 remain open during the sampling process so that residual gases or aerosols within the sample tubes 11 are free to diffuse and mix with each other. Normally the sensitivity of the sampling experiments are not such that each sample tube 11 must be completely isolated from the other sample tubes 11. Nonetheless, if the sensitivity of the experiment requires that individual sample tubes 11 be isolated from the other sample tubes 11, a flapper or check valve 80, such as shown in FIGS. 10 and 11 may be utilized to effectively close off the open ends of the sample tubes. The check valve 80 is designed to closely fits over the open end of a sample tube 11 and open only when the inlet port 16 is opened such that the force of the incoming ambient air pushes the valve 80 open. At other times the check valve 80 remains closed and prevents diffusion and mixing of gases and aerosols from one sample tube 11 into another.

The check valve 80 is generally cylindrically-shaped and includes an open and a closed end. The closed end of the check valve 80 includes a small hole which functions as an exhaust outlet 81 for the sample tube as the inlet port 16 is opened and ambient air drawn through the gas sampler 10. The check valve 80 includes a rectangularly-shaped elastomer flapper 82 attached at one end to the external surface of the closed end of the check valve 80 to displaceably underlie and cover the exhaust outlet 81. As shown in the drawings, a spring 83 is rivetted or otherwise appropriately secured to the underside of the check valve 80 which lightly pushes or biases the flapper 82 against the body of the valve 80 to close the exhaust outlet 81. The open end of the check valve 80 removably engages the open end of a sample tube 11, and a resilient o-ring 84 positioned within the annular interior grove 85 of the check valve 80 allows an air-tight seal to be formed between the valve 80 and the sample tube 11.

The check valve 80 described above, however, prevents air from flowing back into the sample tube 11 during descent as is normally the case and may cause a pressure differential between the sample tube 11 interior and the canister interior 20 to develop. Accordingly, if back pressure presents a problem for maintaining sample.tube 11 integrity, the check valve 80 can be modified to allow some flow back into the sample tube 11 during descent. A small leak hole or nozzle (not shown) placed in the elastomer flapper 82 adjacent the exhaust outlet 81 allows back flow of gases into the sample tube 11 when pressure within the canister interior 20 becomes greater than the pressure within the sample tube 11.

The foregoing description of a preferred embodiment of the invention has been presented for purposes of illustration and description. It is not intended to be exhaustive or to limit the invention to the precise form disclosed. For example the multi-port gas sampler 10 described herein may have more or less than twelve sample tubes 11 or have more than one camming mechanism 14 operating at the same time. The embodiment described herein explains the principles of the invention so that others skilled in the art may practice the invention in various embodiments and with various modifications as suited to the particular use contemplated. It is intended that the scope of the invention be defined by the claims appended hereto.

The embodiments of this invention in which an exclusive property or privilege is claimed are defined as follows:

1. A multi-port gas sampler comprising:
   a flow-through housing defining a sampling chamber and including means for accommodating a flow of gases to be sampled through the housing;
   a sample support plate including apertures extending across and enclosing the sampling chamber within the housing;
   respective gas sampling means depending into the sampling chamber and secured to the sample support plate across each of the apertures in said plate in flow-through relation to the flow of gases through the housing during sampling operations;
   normally closed stopper means mounted on the sample support plate operatively associated with each of the gas sampling means and normally blocking the flow of gases to be sampled through its respective gas sampling means; and
   means for selectively opening the stopper means associated with each of the gas sampling means, said means being mounted on the sample support plate and adapted to rotate under and selectively lift open said stopper means to accommodate a predetermined flow of gases to be sampled through the respective gas sampling means.

2. The gas sampler of claim 1 including means for signalling the opening and closing of the stopper means associated with each of the gas sampling means.

3. The gas sampler of claim 2 including control means for sensing the opening and closing of the stopper means associated with each of the gas sampling means and selectively opening the stopper means to accommodate a predetermined flow of gases through the corresponding gas sampling means.

4. The gas sampler of claim 1 and said means for accommodating a flow of gases to be sampled through the housing being adapted to conduct ambient air through the gas sampling means within the housing.

5. The gas sampler of claim 1 wherein said means for accommodating a flow of gases to be sampled through the housing includes a fluid pumping means to draw a predetermined volume of gas through the housing.

6. The gas sampler of claim 1 wherein said means for selectively opening the stopper means associated with each of the gas sampling means includes a camming mechanism adapted to rotate under and lift open the stopper means associated with each of said gas sampling means.

7. The gas sampler of claim 1 wherein the means for selectively opening the stopper means associated with each of the gas sampling means includes a drive motor to drive said means for selectively opening the stopper means.

8. The gas sampler of claim 1 including guard means attached to the housing and positioned external to the sampling chamber to enclose and protect the sample support plate, the stopper means and means for selectively opening said stopper means.

9. The gas sampler of claim 1 wherein said gas sampling means includes a check valve for retarding the flow of gases into the gas sampling means from the sampling chamber to essentially isolate the sampling means within the chamber when its respective stopper means is in its normally closed position.

10. The gas sampler of claim 9 wherein said check valve includes means for allowing a back-flow of gases into the gas sampling means from the sampling chamber when the gas pressure in the sampling chamber is greater than the gas pressure in the gas sampling means.

11. The gas sampler of claim 1 wherein said gas sampling means include capillary tubes to facilitate the flow of gases into the sampling chamber.

12. A multi-port gas sampler comprising:
a flow-through housing defining a sampling chamber and including gas outlet means to accommodate a flow of gases to be sampled through the housing;
a sample support plate including apertures extending across and enclosing the sampling chamber within the housing;
respective gas sampling tubes depending into the sampling chamber and secured to the sample support plate across each of the apertures in said plate in flow-through relation to the flow of gases through the housing during sampling operations;
normally closed stopper means mounted on the sample support plate operatively associated with each of the gas sampling tubes and normally blocking the flow of gases to be sampled through its respective gas sampling tubes;
a camming mechanism mounted on the sample support plate adapted to rotate under and selectively lift open the stopper means associated with each of said gas sampling tubes to accommodate a predetermined flow of gases to be sampled through the respective gas sampling tubes;
a drive motor carried by the sample support plate adapted to rotate said camming mechanism; and
signalling means mounted on the sample support plate aligned with the stopper means and associated with each of the gas sampling tubes such that a signal is sent when said stopper means is selectively opened by the camming mechanism.

13. The gas sampler of claim 12 including fluid pumping means connected to the gas outlet means of the flow-through housing to facilitate a flow of gases through the housing.

14. The gas sampler of claim 12 including control means for sensing the signal sent by the signalling means and selectively operating the drive motor such that the rotation of the camming mechanism selectively opens the stopper means associated with each gas sampling tubes to accommodate a flow of gases through the corresponding gas sampling tube and the flow-through housing.

15. The gas sampler of claim 12 and each of said gas sampling tubes being adapted to retain removable gas sampling adsorbent material in flow-through relation.

16. The gas sampler of claim 12 and each of said gas sampling tubes being releaseably secured to said sample support plate.

* * * * *